(12) United States Patent
Freese

(10) Patent No.: US 10,136,932 B2
(45) Date of Patent: Nov. 27, 2018

(54) SPINAL PLATE AND DISTRACTION/COMPRESSION PIN SYSTEM

(71) Applicant: Camber Spine Technologies, LLC, Wayne, PA (US)

(72) Inventor: Andrew Freese, Coatesville, PA (US)

(73) Assignee: Camber Spine Technologies, LLC, Wayne, PA (US)

( * ) Notice: Subject to any disclaimer, the term of this patent is extended or adjusted under 35 U.S.C. 154(b) by 628 days.

(21) Appl. No.: 14/703,279

(22) Filed: May 4, 2015

(65) Prior Publication Data

US 2015/0230841 A1 Aug. 20, 2015

Related U.S. Application Data

(63) Continuation-in-part of application No. 12/973,685, filed on Dec. 20, 2010, now abandoned.

(51) Int. Cl.
*A61B 17/80* (2006.01)
*A61B 17/70* (2006.01)
(Continued)

(52) U.S. Cl.
CPC ...... *A61B 17/8052* (2013.01); *A61B 17/7059* (2013.01); *A61B 17/8004* (2013.01); *A61B 17/846* (2013.01); *A61B 17/8009* (2013.01); *A61B 17/8014* (2013.01); *A61B 2017/681* (2013.01)

(58) Field of Classification Search
CPC ............ A61B 17/1739; A61B 17/7059; A61B 17/80; A61B 17/8004; A61B 17/8009; A61B 17/8014; A61B 17/8019; A61B 17/8033; A61B 17/8047; A61B 17/8052; A61B 17/8061; A61B 17/808; A61B 17/846; A61B 17/86; A61B 17/8625; A61B 17/8635; A61B 17/8645; A61B 17/8685; A61B 17/885; A61B 17/8897; A61B 2017/681; A61B 2017/90

See application file for complete search history.

(56) References Cited

U.S. PATENT DOCUMENTS 6,355,038 B1 3/2002 Pisharodi
7,618,418 B2 11/2009 Malandain
(Continued)

FOREIGN PATENT DOCUMENTS

DE 4201043 7/1993
FR 2865376 7/2005

*Primary Examiner* — Kevin T Truong
*Assistant Examiner* — Tracy Kamikawa
(74) *Attorney, Agent, or Firm* — Pabst Patent Group LLP

(57) ABSTRACT

Fusion plates and interbody fusion devices have been developed that contain slots to allow the use of pins to position and to guide the placement of the plate while the screws are being secured, reducing the likelihood of improper placement and localization of the plate and screws. The slots contain ridges formed of a plurality of teeth that are configured to engage with corresponding ridges and teeth on the shaft of a distraction pin. After the plate is placed over the distraction pins, the plate is immobilized in the inferior and superior directions and also in the anterior-posterior direction even prior to placement of the bone screws in the plate. Optionally, the pins may be compressed together to apply compression to the vertebra prior to placement of the bone screws.

9 Claims, 19 Drawing Sheets

(51) Int. Cl.
*A61B 17/84* (2006.01)
*A61B 17/68* (2006.01)

(56) References Cited

U.S. PATENT DOCUMENTS

| | | | |
|---|---|---|---|
| 7,749,256 B2 * | 7/2010 | Farris | A61B 17/8009 606/282 |
| 2002/0151896 A1 | 10/2002 | Ferree | |
| 2003/0055430 A1 | 3/2003 | Kim | |
| 2003/0158556 A1 | 8/2003 | Taras | |
| 2005/0096657 A1 * | 5/2005 | Autericque | A61B 17/7059 623/17.11 |
| 2006/0264948 A1 | 11/2006 | Williams | |
| 2007/0123884 A1 | 5/2007 | Abdou | |
| 2010/0152781 A1 | 6/2010 | Nehls | |

* cited by examiner

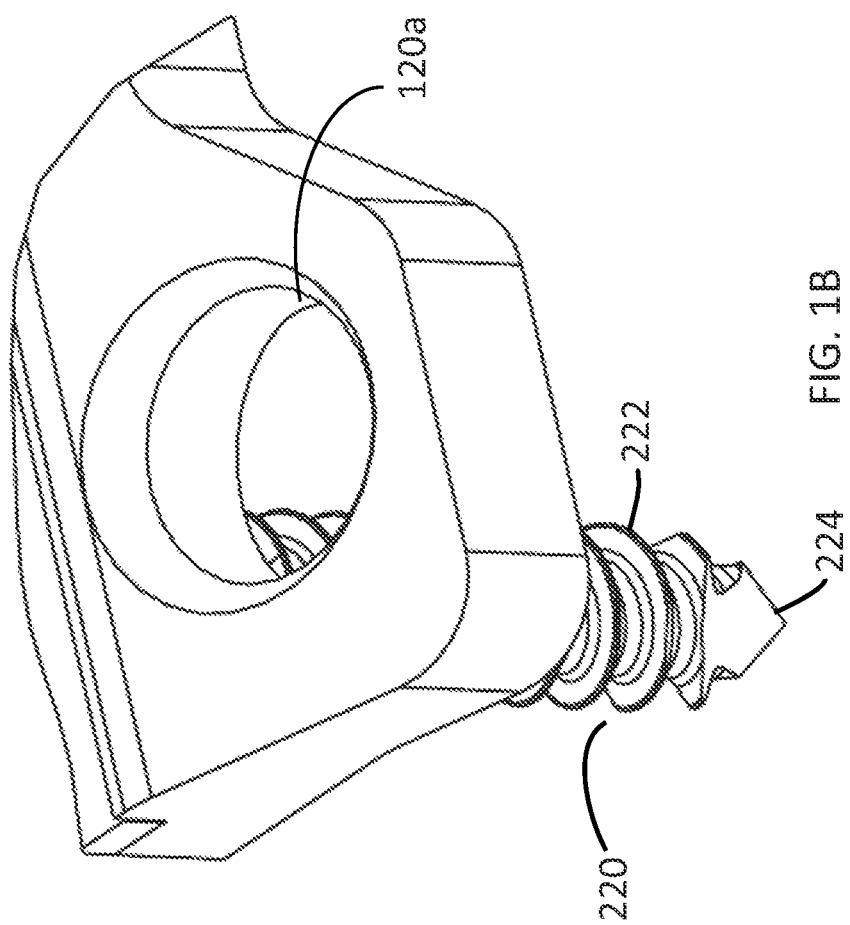

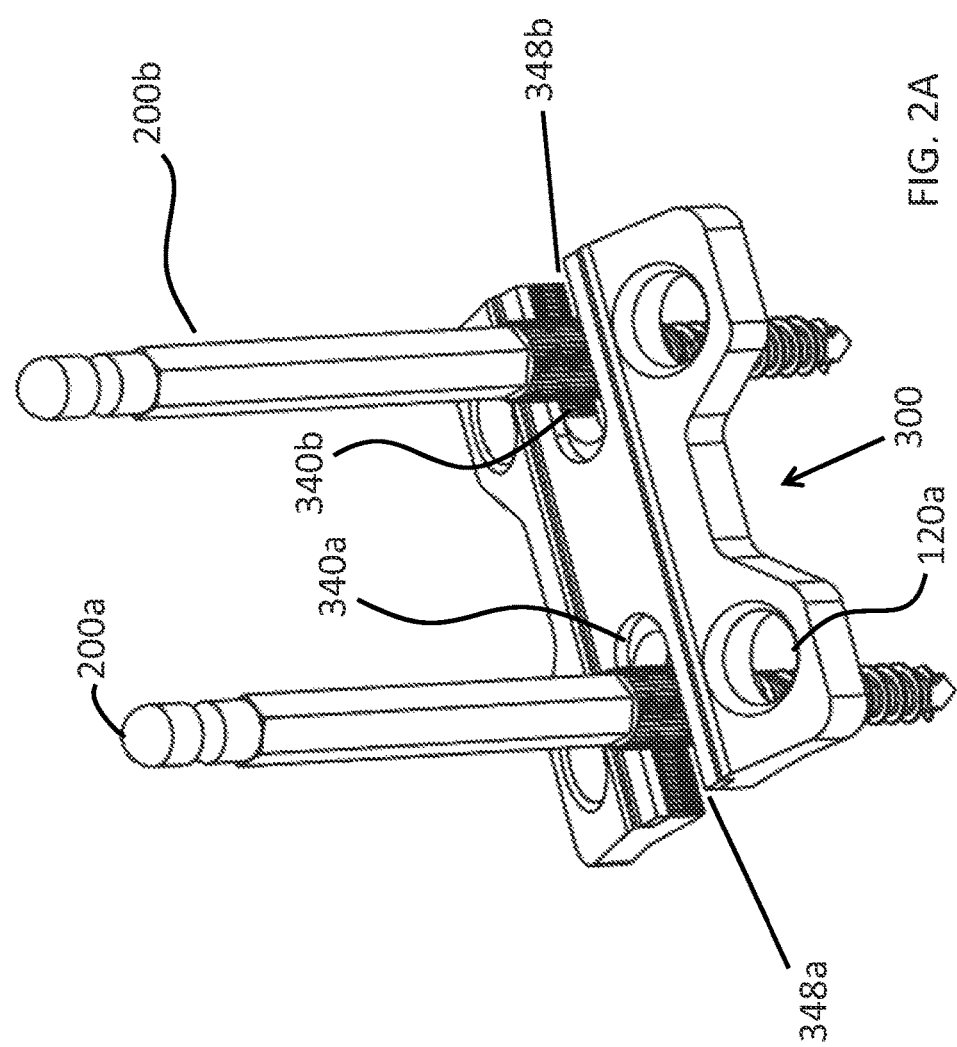

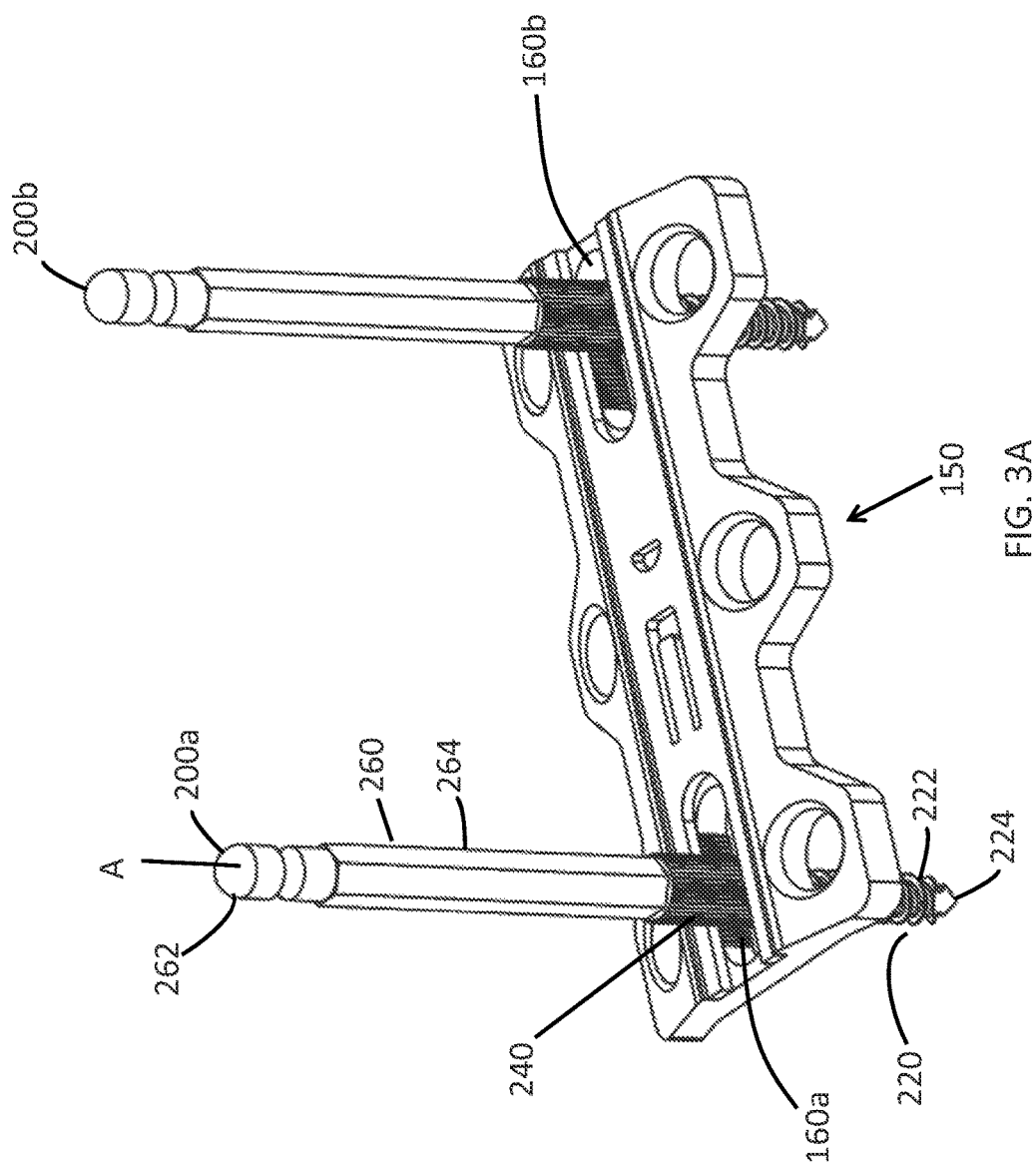

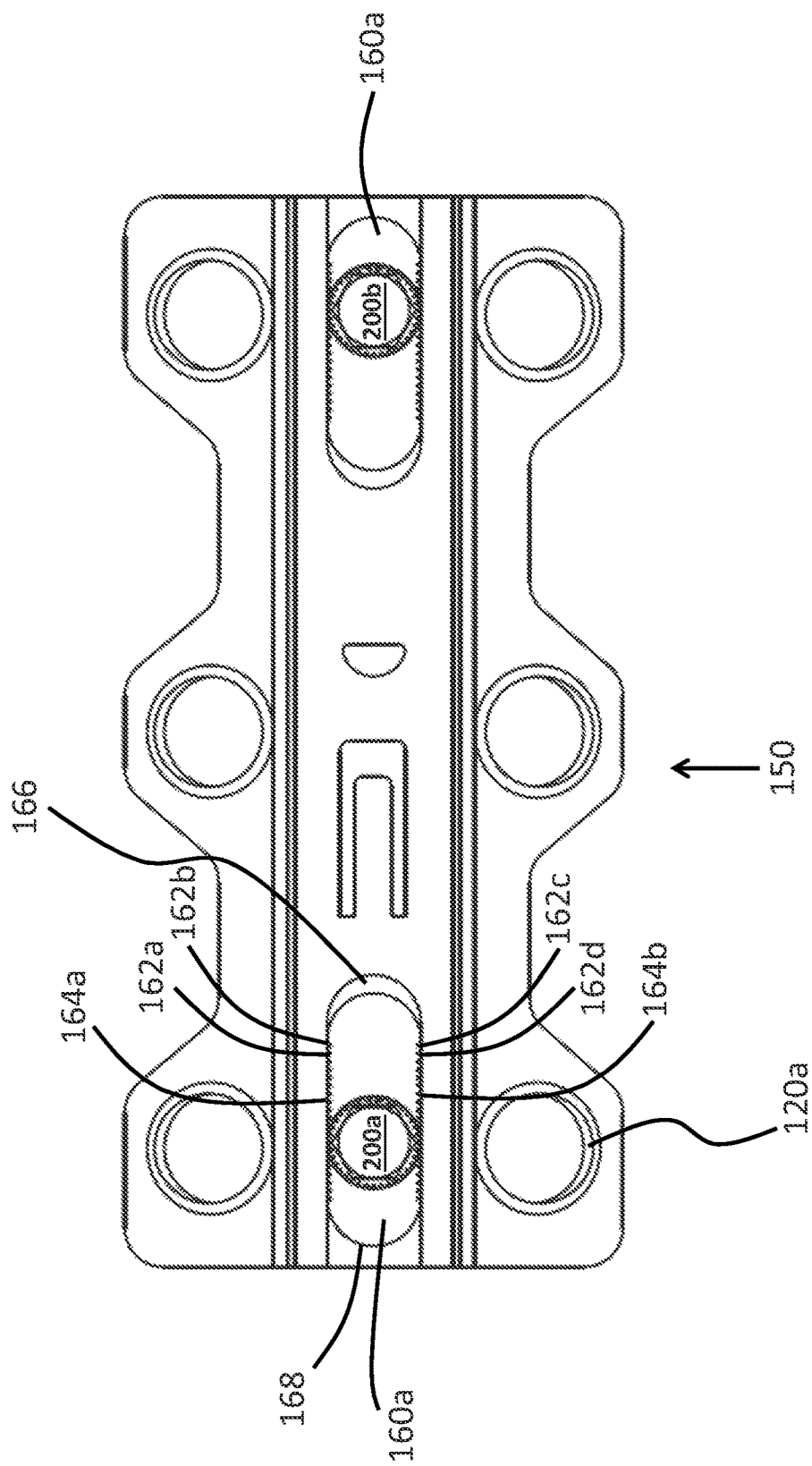

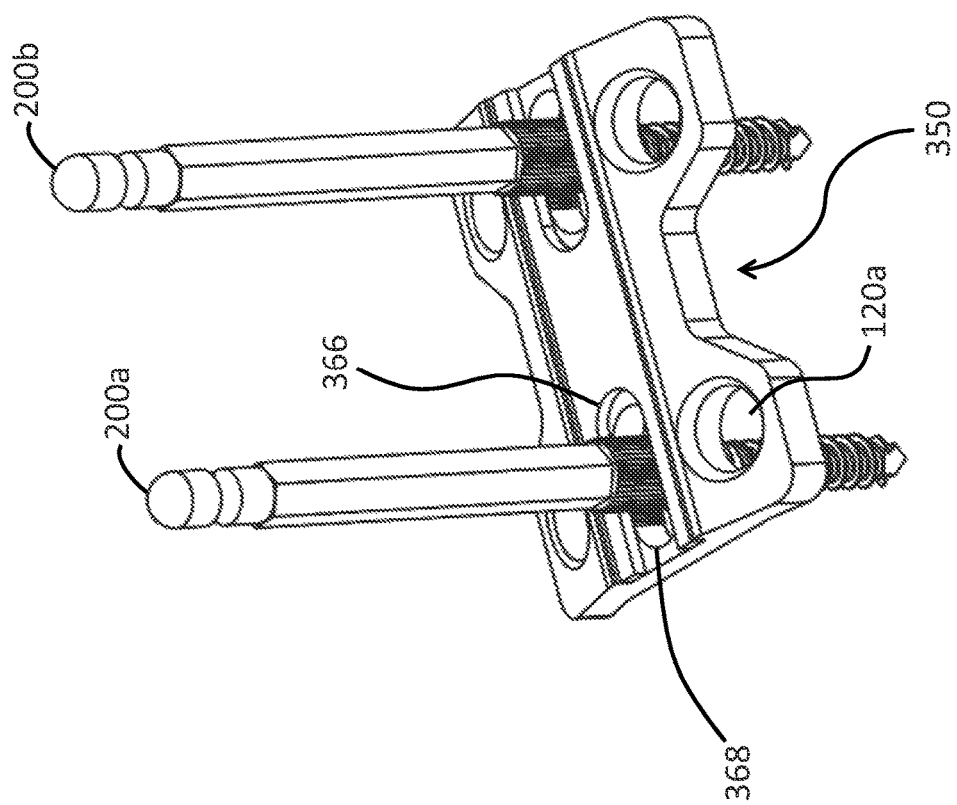

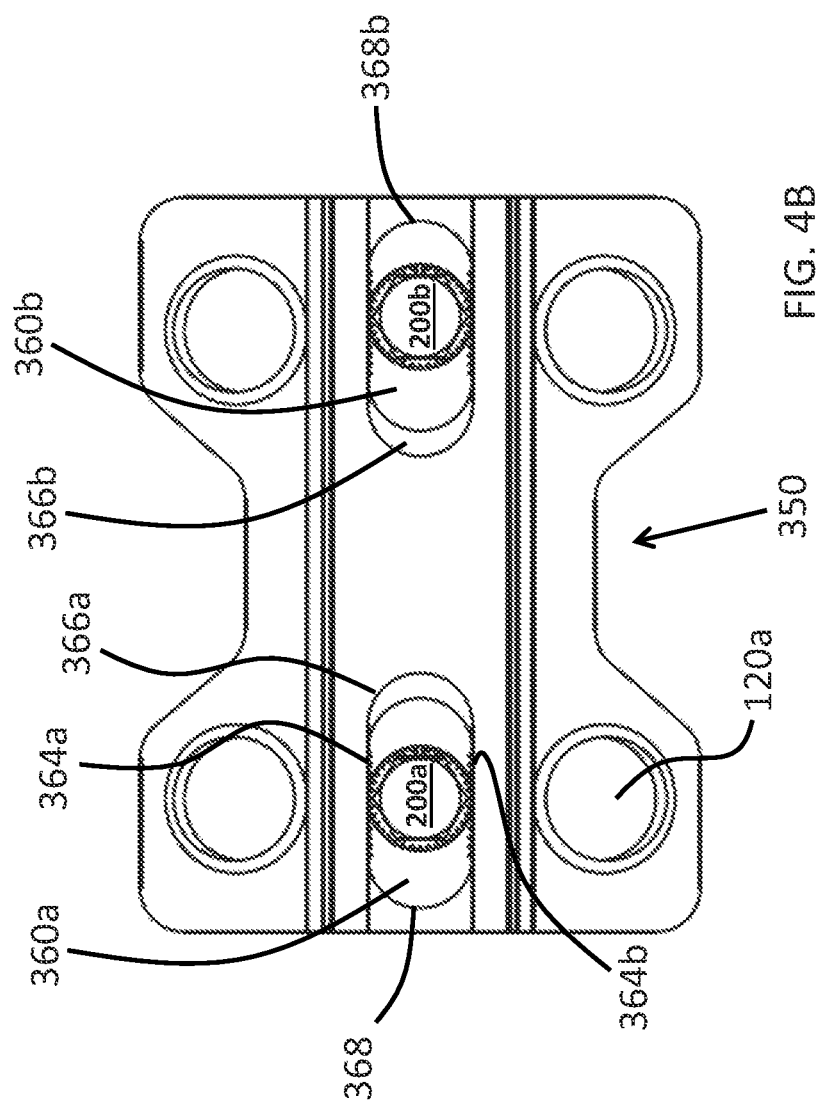

SPINAL PLATE AND DISTRACTION/COMPRESSION PIN SYSTEM

CROSS-REFERENCE TO RELATED APPLICATIONS

This application is a continuation in part application of U.S. application Ser. No. 12/973,685, filed Dec. 20, 2010, the disclosure of which is incorporated by reference in its entirety.

FIELD OF THE INVENTION

This invention relates to devices used in the stabilization and fusion of spinal vertebrae during and after spine surgery, and more specifically, relates to systems and methods for using a fusion plate for stabilizing vertebrae as part of a corpectomy or discectomy procedure to allow bone growth to occur.

BACKGROUND OF THE INVENTION

Fusion plates are used to immobilize and fuse adjacent spinal vertebrae following a discectomy (spinal disc removal) or for immobilizing the area surrounding a corpectomy (removal of an entire vertebral body). Examples of fusion plates presently existing in the art are those produced by Medtronic Inc., Dupuy AcroMed, Inc., and Globus Medical, Inc., to name a few.

Discectomy and corpectomy procedures create a gap in the spine from the removed disc or vertebral body. Typically the gap is closed by inserting a bone graft or bone graft substitute. The adjacent vertebrae surrounding the discectomy or corpectomy site are then immobilized by attaching a fusion plate, usually on the anterior side of the spine, so that the vertebrae fuse to the bone graft, forming an entire fused section of the spine. Fusing the vertebrae to the bone graft requires that the vertebrae remain immobile.

Presently, in performing a discectomy or corpectomy, a distractor is used to spread the adjacent vertebrae so that the disc or vertebral body of interest can be removed. In use, a pair of distractor pins, which are essentially screws having a head for engaging with the distractor, are screwed into the vertebrae adjacent to the discectomy or corpectomy site. One pin is placed in the upper vertebra, and a second pin is placed in the lower vertebra, both vertebrae being directly adjacent to the discectomy or corpectomy site. The distractor is then coupled to the pins on the upper and lower vertebrae, above and below the site, and the vertebrae are then mechanically spread apart, for aiding in the removal of any remaining portion of the deteriorated disc or vertebral body, and also to create a gap for placing a bone graft.

Once the bone graft is placed, the distractor is removed. The distractor pins are then removed from the spine and a fusion plate is placed in a position keeping the adjacent upper and lower vertebrae as well as the bone graft immobilized. The plate is screwed into the upper and lower vertebrae.

Cervical fixation devices are commonly used to stabilize the cervical spine and promote successful bony fusion. Cervical fixation devices, including plate/screw devices, have been described for both the anterior and posterior application to the cervical spine. In spite of this, however, the available cervical plating systems have certain features that limit their usefulness in cervical spine reconstructive surgery. First, application of the available cervical plates requires a number of complex steps during surgery. Often, due to cumbersome instrumentation, application of a cervical plate may necessitate unnecessary steps to correctly size and apply the plate to the spine. Second, cervical plating systems often prevent accurate visualization of the bone graft/vertebra junction thus obscuring accurate placement of the cervical plate. Third, cervical plating systems often do not allow for compression of the bone graft, a step that is important in promoting bony fusion. Fourth, cervical plating systems generally use a cumbersome mechanism with several steps to prevent back out of the screws from the plate. Fifth, many cervical systems do not allow variability in placement of cervical screws and thus are not adaptable to anatomic variations in the cervical vertebra.

Moreover, current anterior cervical plating systems require the prior removal of the distractor pins placed in the vertebral bodies for distraction of the disc space during surgery and placement of the graft. This means that precise information about the localization of the vertebral bodies, their geometry and dimensions, which is garnered at the outset of the case during the placement of the pins, is lost. After the pins are removed at the end of the case, and frequently bone wax introduced to prevent bleeding from the pin sites, a plate is selected and introduced, typically by placing screws into the vertebral bodies above and below the fusion mass (graft). Error is introduced during this somewhat clumsy process, and the holes where the pins had been placed have to be avoided by the screws, for fear that entering the holes might not allow optimum securing of the screws.

Another problem associated with current anterior cervical plate systems is that placing the plate typically reduces the load across the fusion plane. However, it is known that bones fusion together better when there is a load applied across the fusion or fracture line.

U.S. Patent Application No. 2007/0123884 to Abdou describes different bone fixation systems which utilize distraction screws and fusion plates. Some of Abdou's proposed designs include a modular distraction screw, including a distal segment that can remain in the bone after a discectomy procedure and during plating. Abdou alleges that after a plate is lowered onto these distal segments, the head of these screws can be rotated to immobilize the plate. However, the design of these screws does not allow for true immobilization of the plate while it is being secured. Further, none of Abdou's proposed designs are able to provide compression (or distraction) along the axis of the fusion plate prior to securing the plate with bone screws.

Therefore, a need exists for a fusion plate system and method which allows a section of spine to be precisely compressed following a corpectomy or discectomy, so that sufficient and optimal immobilization and spinal fusion can occur.

There is a further need for a fusion plate system and method that allows a surgeon greater freedom to use both of his or her hands during placement of bone screws in a fusion plate.

SUMMARY OF THE INVENTION

Modified anterior fusion plates and interbody fusion devices have been developed that contain slots to allow the use of pins to position and to guide the placement of the plate while the screws are being secured, reducing the likelihood of improper placement and localization of the plate and screws. The slots contain ridges or teeth which are configured to engage with corresponding ridges or teeth on the shaft of a distraction pin. After the plate is placed over the distraction pins, the ridges or teeth on the pins are aligned to the corresponding ridges or teeth on the slots in the plate to temporarily immobilize the plate onto the pin. This immobilizes the plate in the inferior and superior directions and also in the anterior-posterior direction even prior to placement of the bone screws in the plate.

Additionally, after locking the pins within the slots of the fusion plate, there is sufficient give that the pins may be compressed together to apply compression to the vertebra prior to placement of the bone screws.

Alternatively, the pins may be adjusted to further distract the disc space, prior to insertion of the bone screws, if needed.

This system allows a surgeon greater precision when placing the bone screws because the surgeon does not have to use one hand to keep the fusion plate in position while positioning the plate and inserting the bone screws. Rather the surgeon can use both hands, if needed, during placement of the bone screws. Additionally, this system eliminates the need for using a separate plate introducer or plate holder during placement of the bone screws. Finally, the system described herein reduces the amount of time required for the operative procedure, and prevents inadvertent introduction of the bone screws for the plate into the former pin holes.

This system allows the surgeon to carefully identify the geometry of the vertebral bodies at the outset of the case, when there is no significant bleeding, and when the field is clearly visualized, to determine the placement of the distraction pins. Then, the careful placement of the distraction pins serves as the guide and basis for placement of the plate and screws.

BRIEF DESCRIPTION OF THE DRAWINGS

FIGS. 1A-1D are different views of a two level cervical plate with two pins. FIG. 1A is a perspective view of the plate with pins. FIG. 1B is a magnified view of a borehole in the plate, which corresponds with the region A circled on FIG. 1A. FIG. 1C is a top view of the plate with pins. FIG. 1D is a magnified view of one slot and pin in the plate, which corresponds with the region B circled on FIG. 1C.

FIGS. 2A and 2B are different views of a one level cervical plate with two pins. FIG. 2A is a perspective view of the plate with pins. FIG. 2B is a top view of the plate with pins.

FIGS. 3A and 3B are different views of a two level cervical plate containing two closed slots with two pins. FIG. 3A is a perspective view of the plate with pins. FIG. 3B is a top view of the plate with pins.

FIGS. 4A and 4B are different views of a one level cervical plate containing two closed slots with two pins. FIG. 4A is a perspective view of the plate with pins. FIG. 4B is a top view of the plate with pins.

FIG. 5A is a perspective view of the pin. FIG. 5B is a magnified view of the ridged portion and the bone entry portion, which corresponds with the region C circled on FIG. 5A.

FIG. 6A is a perspective view of the plate with pins. FIG. 6B is a top view of the plate with pins.

FIG. 7A is a perspective view of the plate with pins. FIG. 7B is a top view of the plate with pins.

FIG. 8A is a perspective view of the plate with pins. FIG. 8B is a top view of the plate with pins.

FIG. 9A is a perspective view of the plate with pins. FIG. 9B is a top view of the plate with pins.

DETAILED DESCRIPTION OF THE INVENTION

I. Plate and Pin System

Figure 1A:
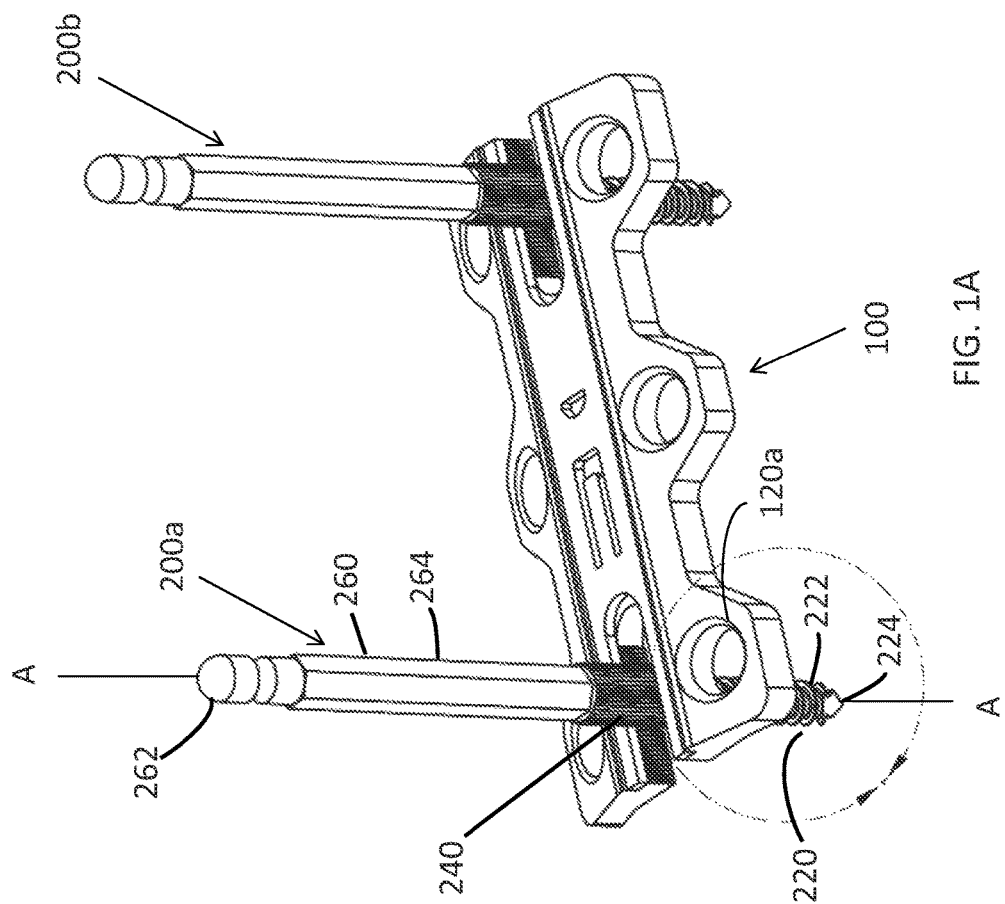

Placement of a distraction pin early in the course of an anterior cervical spine operation is commonly done to allow accurate distraction of the disc space and promote a thorough decompression of the spinal cord and nerve roots. The distraction pins are generally placed in the midline of the vertebral body at a 90° angle to the vertebra. This position is ideal for reference throughout the operation. Because the distraction pins are placed early in the operation, prior to distortion of the anatomy by surgical dissection, they represent the most accurate reference site for placement of an anterior cervical plate.

An anterior cervical plating system has been designed to reference the size and location of the cervical plate from the distraction pins in the vertebral body. The distraction pins serve several functions besides vertebral distraction during decompression, allowing correct sizing of the plate, compression of the bone graft during plating and provisionally securing the plate during drilling of the screw holes and application of the screws. In this way, the surgeon can move immediately from the decompression to grafting and plating without the need of removal of the distraction pins. The distraction pins provide rapid and accurate information on the size of the plate and allow graft compression and provisional plate fixation. A series of complex surgical steps is simplified into a simple exercise using the distraction pins in this way.

Plates and pins are preferably made of surgical stainless steel or titanium. Alternatively, plates can also be made of biocompatible polymers, such as biodegradable or non-biodegradable polymers. Most other materials lack sufficient strength under stress.

These plates and pins, systems thereof, and methods for installing this system upon a patient's spine, overcome the drawbacks of the prior art by allowing a desired level of compression to be applied to the adjacent vertebrae surrounding the site of a corpectomy or discectomy, prior to, and during, the anchoring of the fusion plate. Alternatively, if needed, a surgeon can distract the vertebrae using this system, after placement of the plate. Furthermore, the fusion plate system and method results in the fusion plate being properly centered upon a patient's spine, so that an aesthetically pleasing, as well as functional, surgical result is achieved.

A. Fusion Plate

Fusion plates, including at least two slots for receiving the distraction pins and four or more boreholes for receiving bone screws, are described herein. In some embodiments, the plate includes a third slot for receiving bone screws, which is located between the other two slots. Optionally, the plate contains more than three slots, where one slot is located at each end and the other slots are located along the length of the plate, between the slots at the ends. These embodiments are useful for multi-level plates, which fit over two levels or more in the spine (i.e. connecting three vertebral bodies or more than three vertebral bodies).

The fusion plate is typically an elongated plate. Generally, the plates are long enough to fit over at least two vertebrae and one disc space involved in spinal fusion surgery. Due to diversity in spinal anatomies, typically a system contains a variety of different sized spinal fusion plates having different dimensions so that the appropriate sized plate can be selected for a given patient and site.

The fusion plates include slots for receiving the distraction pins and boreholes for receiving bone screws. In some embodiments, the fusion plates contain one or more window regions for visualizing junctions between two vertebrae.

FIGS. 1A-1D is an illustration of an exemplary spinal fusion plate with two slots and two distraction pins in the slots. This fusion plate is configured to fuse two levels of the cervical spine together (i.e. three vertebral bodies and two disc spaces).

Figure 1C:
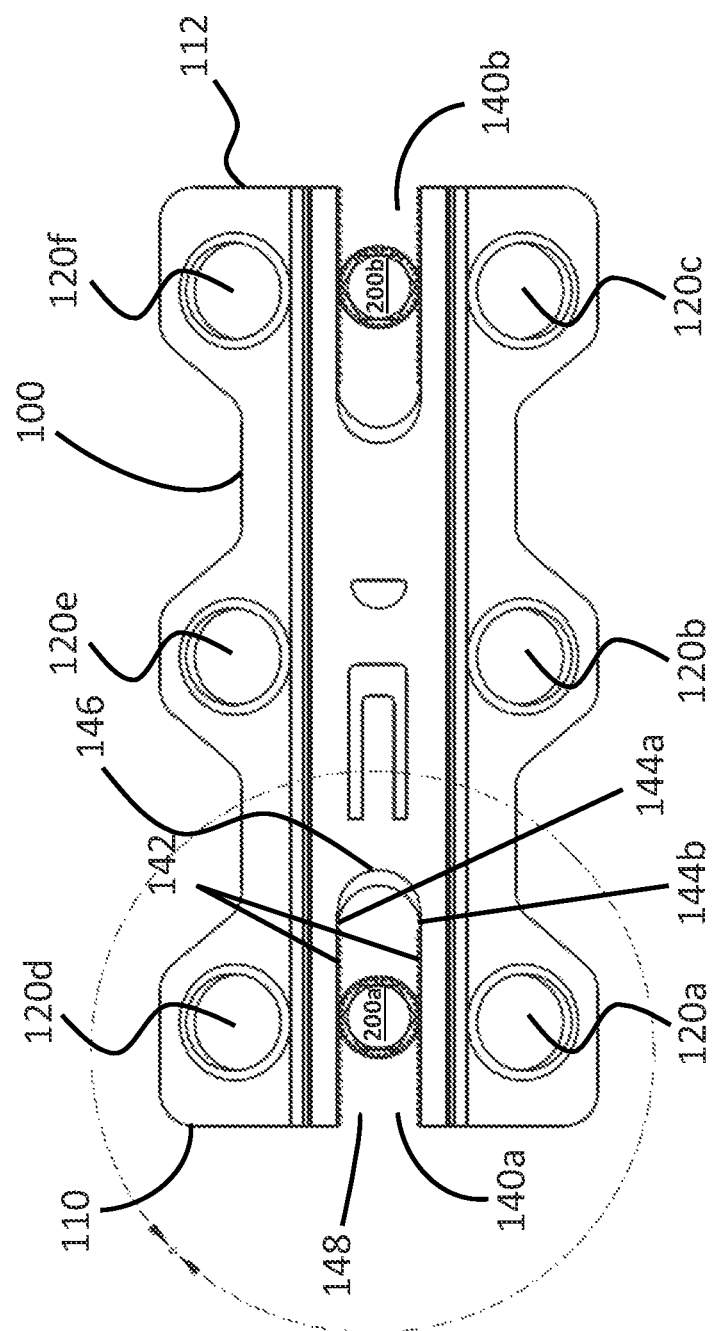
Figure 1D:
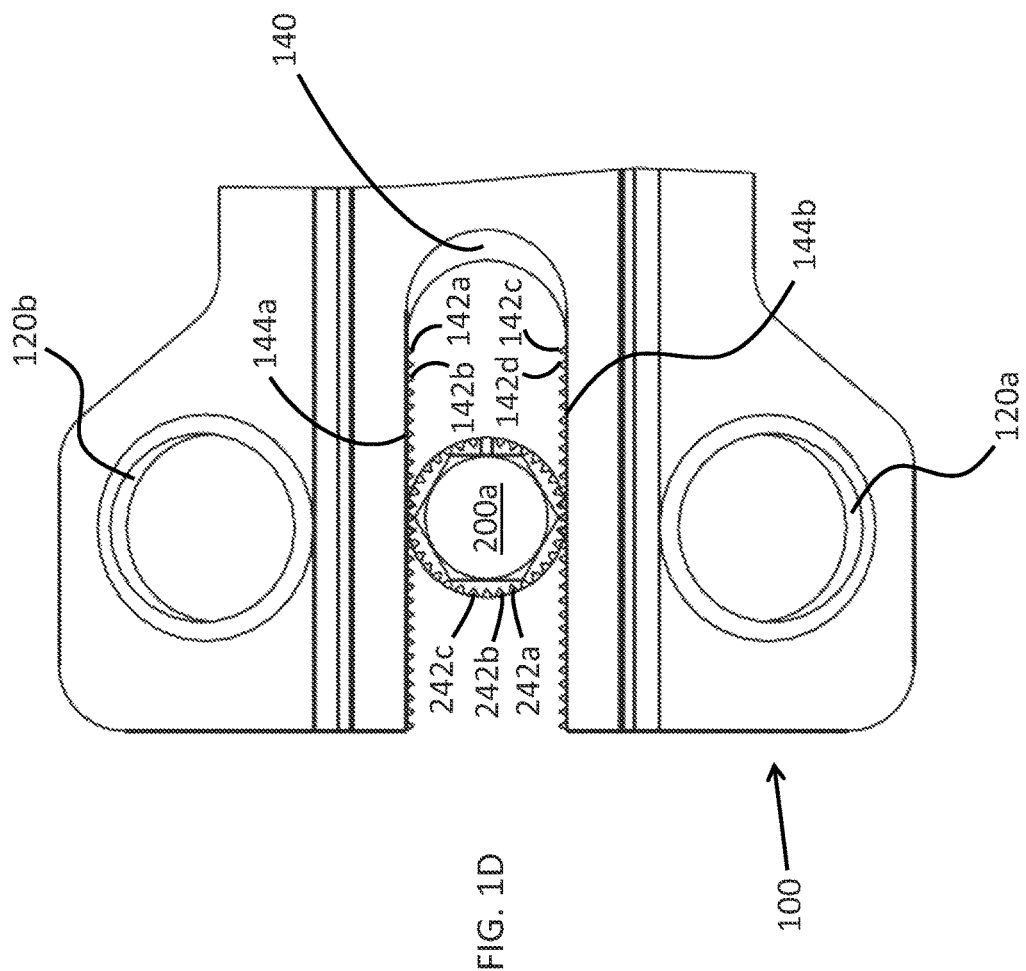

As shown in FIGS. 1A and 1C, the plate 100 has holes 120a, 120b, 120c, 120d, 120e, and 120f, for screws to secure the plate 100 to the vertebrae. The plate has slots 140a and 140b for placement of distraction pins 200a and 200b. The slots 140a, 140b allow placement, manipulation, and removal of pins after insertion of screws through holes 120a-120f.

The shape of the fusion plates and positions and numbers of holes for bone screws for the plates depicted in the Figures are merely illustrative. One of skill in the art would understand that fusion plates having different shapes and sizes can be modified to contain slots with a plurality of teeth configured to mate with a region on a distraction pin containing corresponding teeth, as described herein.

Another embodiment similar to the plate depicted in FIGS. 1A-1D is shown in FIGS. 3A and 3B. These plates 150 have fully enclosed slots 160a and 160b for pin placement.

The fusion plate depicted in FIGS. 1A-1D is configured to fuse two levels of the cervical spine together (i.e. three vertebral bodies and two disc spaces). In alternative embodiments, the fusion plate may be configured (e.g., by having have a suitable length, number of boreholes, and slots) so that it can be used to fuse one level of the cervical spine together (i.e. two vertebral bodies and one disc space). Alternatively, the fusion plate may be configured (e.g., by having have a suitable length, number of boreholes, and slots) so that it can be used to fuse more than two levels of the cervical spine together (i.e. more than three vertebral bodies).

1. Slots

The fusion plate has an adaptation at each end to allow the ends of the plate to be secured by the distraction pins.

The fusion plate typically contains two slots positioned at the superior and inferior ends of the plate. The slots allow for positioning of the plates after placement of the pins but prior to removal. The slots also allow for removal of the pins.

In some embodiments, the slots are fully enclosed. In other embodiments, the slots are open at one end, which corresponds with the inferior or superior end of the plate.

The slots have at least three sides: at least two side walls, which are typically substantially parallel with each other, and a first curved wall connecting the two side walls. Optionally, the slots are enclosed and include a fourth side: a second curved wall connecting the two side walls on the side opposite to the first curved wall, which also corresponds with an end of the plate. In this embodiment, the slots are fully enclosed within the plate.

The side walls of the slots are ridged. The ridges are formed from a plurality of teeth along the surface of the walls. The teeth have a size and shape that matches the size and shape of the teeth on the perimeter of a portion of the distraction pins, such that the teeth on the pins fit in the teeth on the side walls similar to a gear and ratchet, and thereby locking the pins in place.

2. Boreholes

The fusion plate contains four or more boreholes, where each hole is configured to receive a bone screw. The boreholes are configured to provide secure placement of bone screws within the holes, and preferably to prevent the screw from coming out of the hole following initial implantation.

A variety of different features may be incorporated into the boreholes to secure the bone screws. Any suitable locking mechanism can be used to secure the screws in the boreholes. Suitable features include, but are not limited to, changes in diameter throughout the height of the borehole, and threads on the walls of the borehole. In all embodiments, these diverse features provide secure placement of bone screws within the boreholes to prevent removal of the screws over time. The shape of the borehole may be configured to hold the head of the bone screw in the hole. For example, in some embodiments, the diameter of the boreholes varies, such that the diameter at the top or anterior portion is the greatest, while at the bottom or posterior portion, the diameter is much smaller, such that it corresponds with the geometry of the head of a corresponding bone screw. (See, e.g. FIG. 1B)

In some embodiments, the anterior cervical plate has a mechanism to allow variable angulation of a bone screw while allowing the screws to be attached to the plate without the need for separate steps. This includes "expandable bushings" that can rotate in desired directions within the plate. These bushings are internally threaded to allow screws to be placed through the bushings. The screws can thus be angled in a desired direction. The screws are designed with a screw head that expands the bushing during terminal seating of the screw so that the bushing is expanded and fixed in position to the hole in the plate. In addition, the screw head has a shape that prevents it from loosening or backing out once it is well-seated into the expandable bushing.

In some embodiments, the anterior cervical plate may also contain a sliding segment or segments to allow fixation of intervening vertebral bodies with screws. This consists of cross member(s) that can be attached to the lateral structures of the plate. The cross members can be adjusted in position towards the top of bottom of the plate such that they are optimally positioned over an intervening vertebral body.

3. Additional Optional Features

Optionally, the plate incorporates a one or more additional features designed to promote ease of application and flexibility of use during anterior cervical plating. These features include one or more "windows" in the plate to allow visualization of the bone graft, variable angled screws, a simple screw locking mechanism (requiring no additional steps), a sliding segment to allow fixation of intervening vertebral bodies and a reference guide for drilling screw holes that allows accurate placement of the screws based on the position of the distraction pins.

In some embodiments, the anterior cervical plate also contains "windows" over the edges of the bone graft so that the graft/vertebra junction can be visualized accurately during plating.

4. Exemplary Spinal Fusion Plates

The fusion plates depicted in the figures are configured for one or two levels of fusion. However, longer plates can also be modified as described herein to contain two or more ridged slots for mating with corresponding ridged portions on distraction pins.

Exemplary fusion plates for two levels of fusion are depicted in FIGS. 1A-1D, 3A-3B, 6A-6B, 7A-7B, 8A-8B, and 9A-9B. As shown in FIGS. 1A-1D, the slots 140a and 140b in the fusion plate 100 can be open at one end 148 (see also FIGS. 6A-6B and 8A-8B). Alternatively, as shown in FIGS. 3A-3B, the slots 160a and 160b in the fusion plate 150 can be open at closed at both ends 166 and 168 (see also FIGS. 7A-7B and 9A-9B).

Figure 2B:
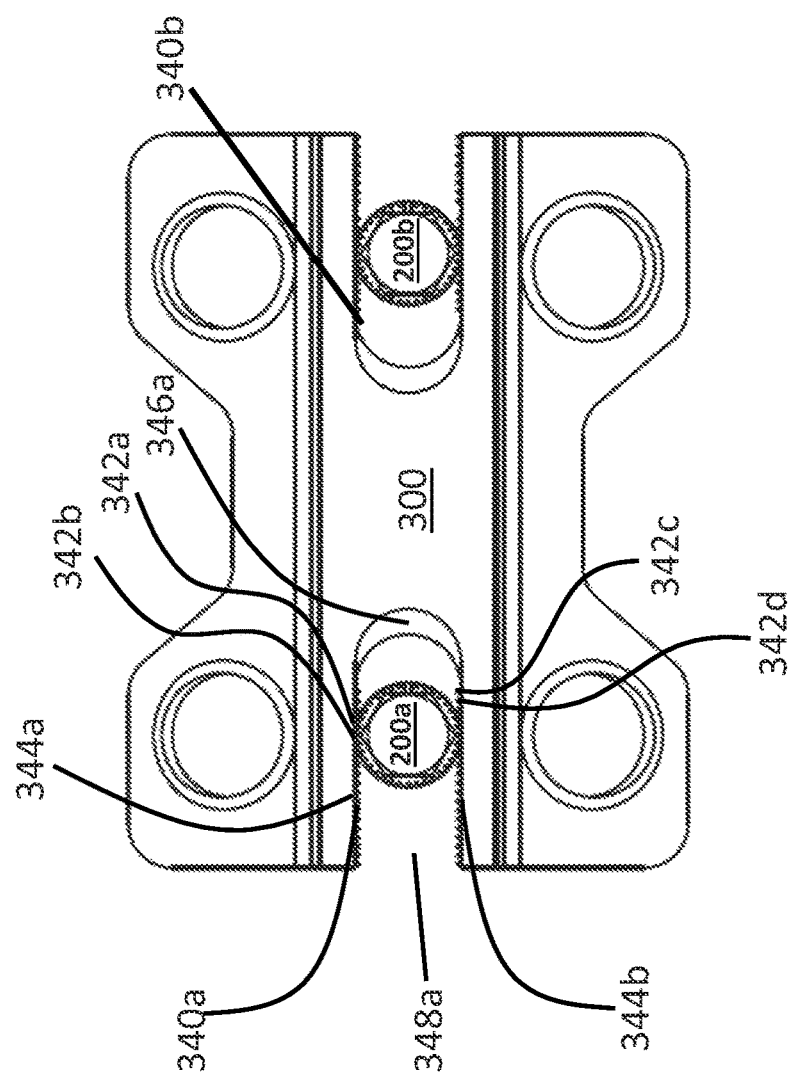

Exemplary fusion plates for one level of fusion are depicted in FIGS. 2A-2B and 4A-4B. As shown in FIGS. 2A-2B, the slots 346a and 346b in the fusion plate 300 can be open at one end 348. Alternatively, as shown in FIGS. 4A-4B, the slots 360a and 360b in the fusion plate 350 can be open at closed at both ends 366 and 368.

a. Fusion Plates with Two Slots for Receiving Pins

An exemplary spinal fusion plate, which serves an anterior cervical plate, is depicted in FIGS. 1A-1D. The fusion plate 100 includes two slots 140a and 140b for receiving the distraction pins 200a and 200b.

The slots have at least three sides: at least two side walls, which are typically substantially parallel with each other, and a first curved wall connecting the two side walls. Each of the slots 140a and 140b has two side walls 144a and 144b, a curved wall 146, and an opening 148 positioned at the end of the plate 110 or 112. The curved wall 146 connects the two side walls 144a and 144b.

The side walls 144a and 144b are ridged and include a plurality of teeth 142a, 142b, 142c and so on, collectively referred to as ridges or teeth 142. The teeth 142 run along the surface of the side walls 144a and 144b. The teeth 142 are configured to connect with corresponding teeth on a portion of the surface of the distraction pin. The length of the teeth 142 corresponds with the depth of the teeth on the corresponding portion of the surface of the distraction pin, such that the teeth on the pins fit in the teeth on the side walls similar to a gear and ratchet, and thereby temporarily locking the pins in place when the plate is placed over the pins.

The fusion plate contains a plurality of boreholes for receiving bone screws. Generally, the fusion plate contains at least four boreholes. The boreholes (e.g., 120a, 120b, 120c, 120d, 120e, and 120f) are configured to receive bone screws. The shape of the boreholes is configured to hold the head of the bone screw in the hole. In some embodiments, the diameter of the boreholes varies, such that the diameter at the top or anterior portion is the greatest, while at the bottom or posterior portion, the diameter is much smaller, such that it corresponds with the geometry of the head of a corresponding bone screw. See, e.g. FIG. 1B.

i. Enclosed Slots

In some embodiments, the slots are enclosed and include a fourth side. For example, as depicted in FIGS. 3A and 3B and 4A and 4B, fusion plates 150 and 350 each include two slots 160a, 160b, and 360a, 360b, respectively, which contain a second curved wall 168a, 168b and 368a, 368b, respectively, connecting the two side walls 164a, 164b and 364a, 364b, respectively, on the side opposite to the first curved wall 166a, 166b and 366a, 366b, respectively, which also corresponds with an end of the plate. In these embodiments, the slots are fully enclosed within the plate.

ii. Windows

Exemplary fusion plates that include one or more windows are illustrated in FIGS. 6A-6B and 7A-7B. As shown in these figures, a window 430 or 470 can be included in a fusion plate 400 or 450 between two slots 440a and 440b or 460a and 460b. Preferred embodiments for including one or more windows in a fusion plate include plates that are used to fuse at least two levels of the spine, such as fusion plates 400 and 450. The plates may contain closed slots (460a and 460b, FIGS. 7A-7B) or open slots (440a and 440b, FIGS. 6A-6B).

b. Fusion Plates with Three Slots for Receiving Pins

In some embodiments, the plate includes a third slot for receiving a pin, which is located between the other two slots. These embodiments are useful for plates that fit over two levels in the spine (i.e. connecting three vertebral bodies).

Exemplary fusion plates containing three slots are depicted in FIGS. 8A-8B and 9A-9B. Each of the fusion plates 500 and 550 includes three slots for receiving distraction pins 200a, 200b, and 200c, where one slot 540a, 540b, or 560a, 560b is located at each end 510 and 512 of the plate, and the third slot 530 or 570 is located substantially in the middle of the plate, such that it generally aligns with the middle set of bore holes 120b and 120d.

Figure 8A:
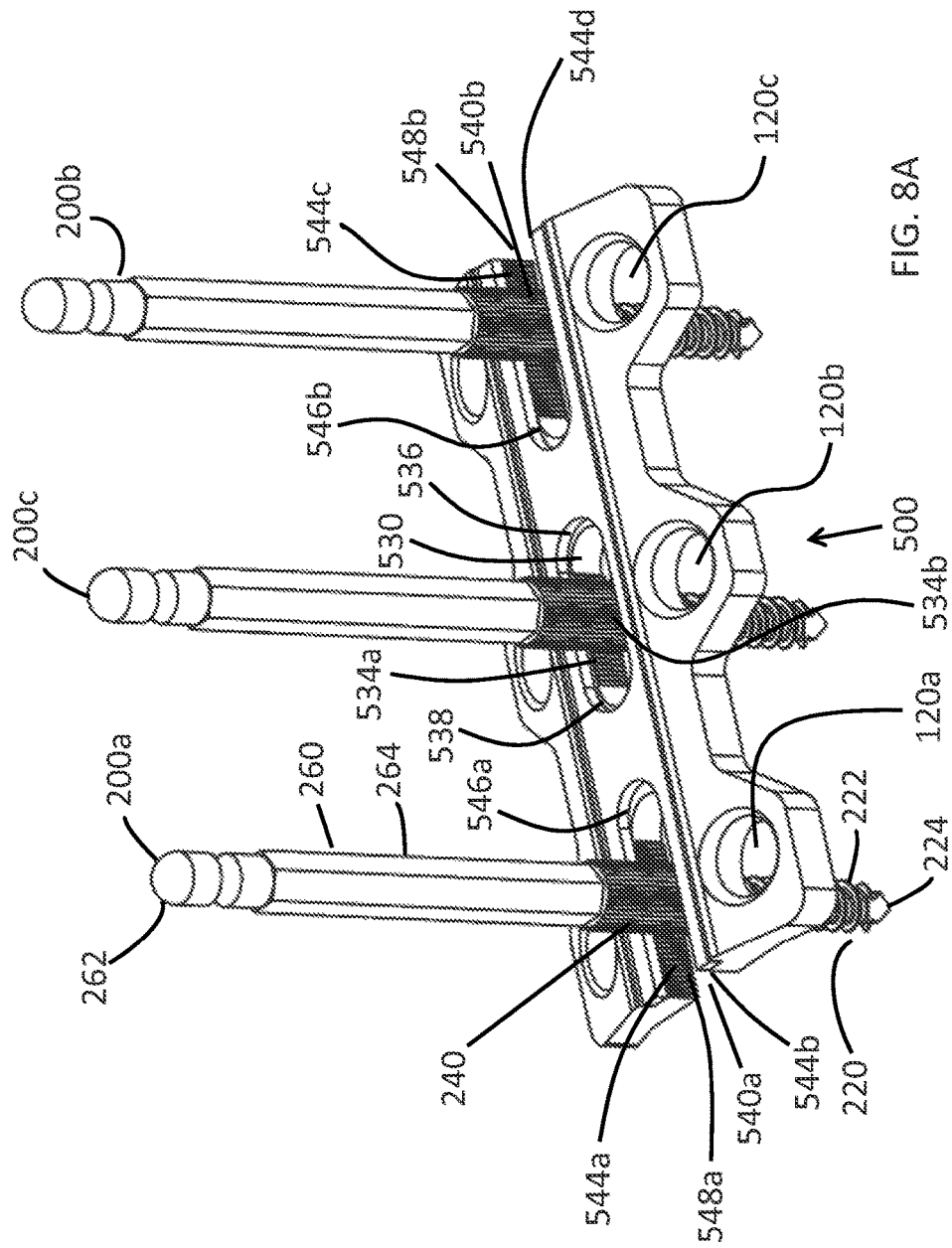
FIGS. 8A and 8B are different views of a two level cervical plate containing three slots with three pins in the slots.
Figure 8B:
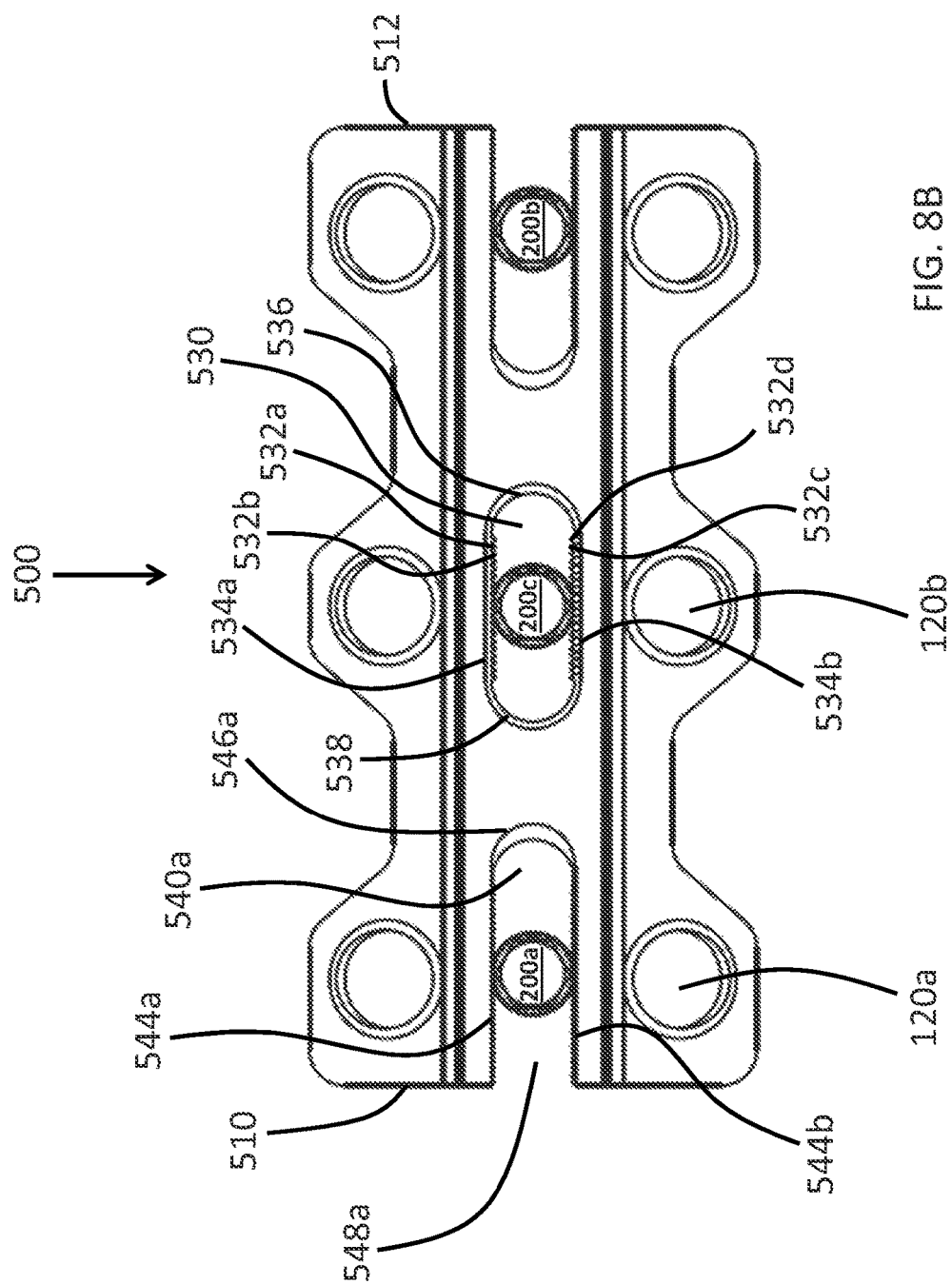
Figure 9A:
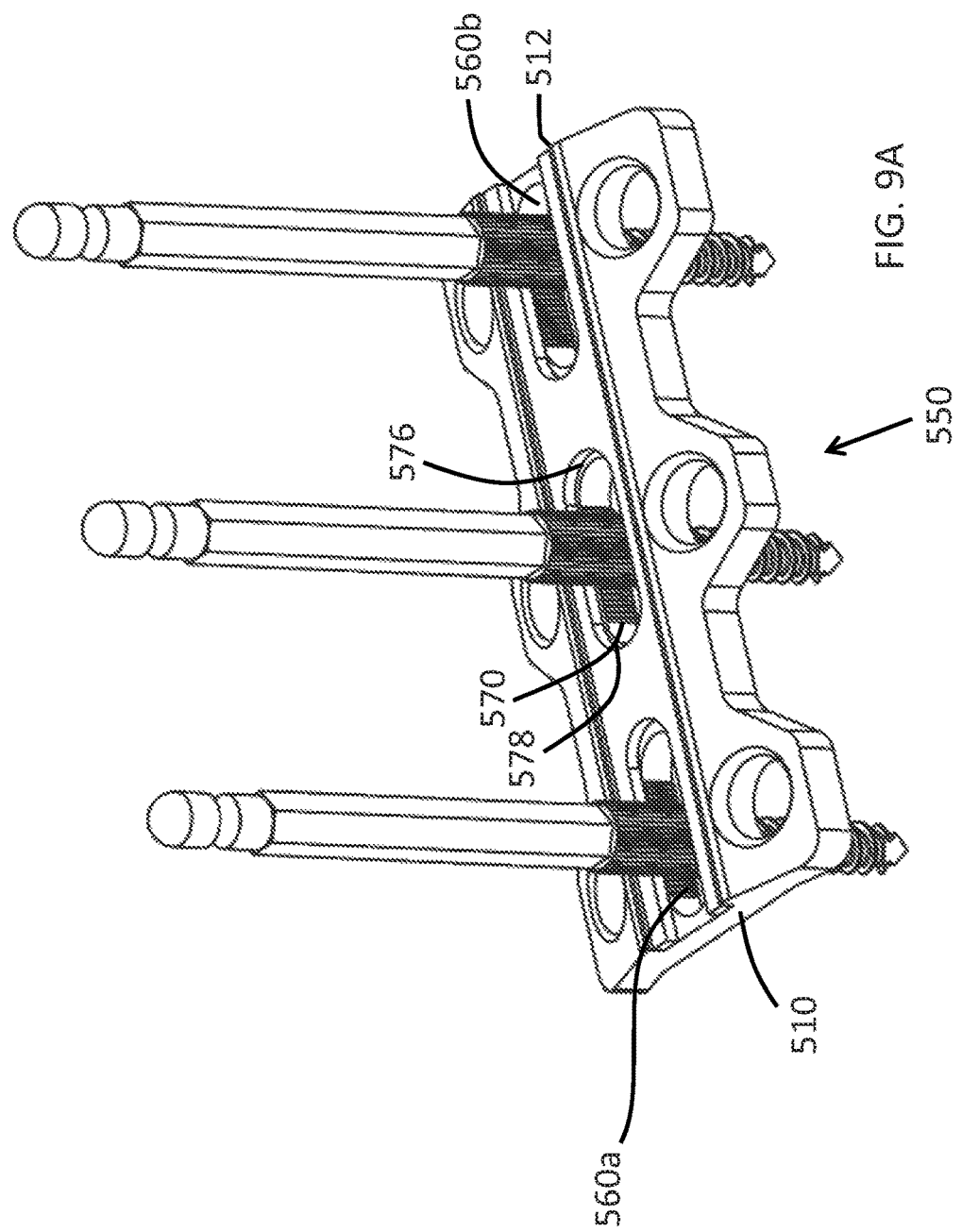
FIGS. 9A and 9B are different views of a two level cervical plate containing three slots, where all of the slots are closed at both ends, with three pins in the slots.
Figure 9B:
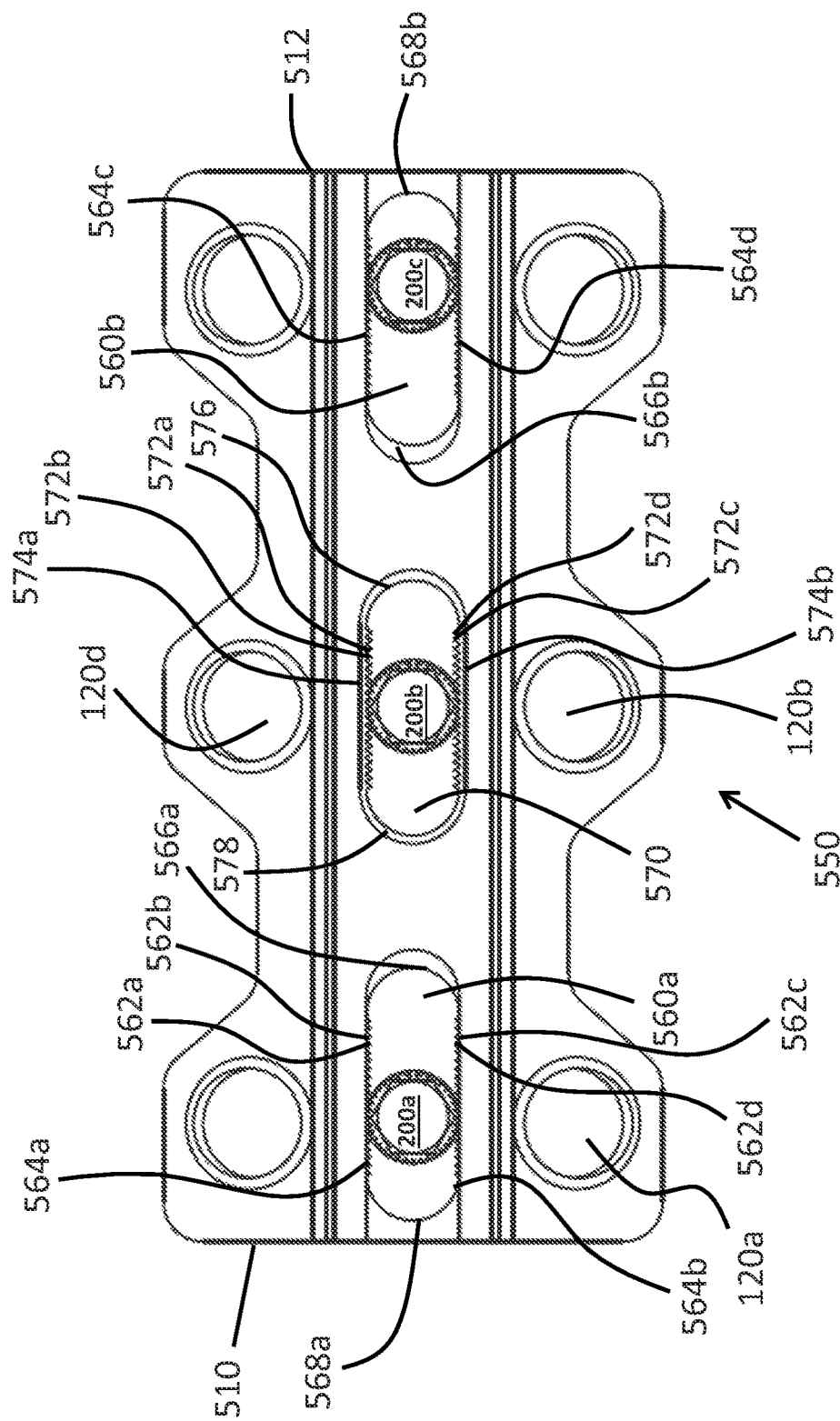

The third slot 530 or 570 in the middle of the plate has two side walls, 534a and 534b or 574a and 574b, which are typically substantially parallel with each other, a first curved wall 536 or 576 and a second curved wall 538 or 578, at each end of the slot, which connect the two side walls. As depicted in FIGS. 8A-8B, the slots 540a, 540b located at each end of the plate are open, such as described above with respect to FIGS. 1A-1D. As depicted in FIGS. 9A-9B, the slots 560a, 560b located at each end of the plate are fully enclosed, such as described above with respect to FIGS. 3A-3B and 4A-4B.

The side walls of all of the slots 544a, 544b, 544c, 544d, 534a, 534b and 564a, 564b, 564c, 564d, 574a, 574b are ridged and include a plurality of teeth 542a, 542b, 542c and so on (532a, 532b, 532c; 562a, 562b, 562c; or 572a, 572b, 572c, respectively), collectively referred to as ridges or teeth 542, 532, 562, or 572, respectively. The teeth 542, 532, 562, or 572 run along the surface of the side walls 544a, 544b, 544c, 544d, 534a, and 534b (FIGS. 8A-8B) or 564a, 564b, 564c, 564d, 574a, and 574b (FIGS. 9A-9B). The teeth 542, 532, 562, or 572 are configured to connect with corresponding teeth on a portion of the surface of the distraction pin 200a, 200b, or 200c. The length of the teeth 142 corresponds with the depth of the teeth on the corresponding portion of the surface of the distraction pin, such that the teeth on the pins fit in the teeth on the side walls similar to a gear and ratchet, and thereby temporarily locking the pins in place when the plate is placed over the pins.

The fusion plates contain a plurality of boreholes for receiving bone screws. When the fusion plates contain three slots, the plate typically contains six boreholes 120a, 120b, 120c, 120d, and 120e.

B. Distraction/Compression Pins

Distraction/compression pins are inserted into the vertebral body, and contain a ridged portion to capture an anterior cervical plate.

The distraction pins currently in use have a broad flange that prevents their removal if a plate is placed on top of the flange. This problem is obviated by the design of the pins described herein to allow placement of the plate with the distractor pin positioned within the veterbral body but still capable of being easily removed.

The distraction pins described herein contain three regions: a threaded bone entry portion, a ridged portion, and a multi-faceted tool fitting region, where the ridged portion is located between the bone entry portion and the tool fitting region. The pins are used to distract the discs and to place the plate. They guide the plate as well as temporarily secure the plate until the screws are positioned. Unlike conventional plates, the pins are not removed until after the plates are secured with the screws. Further, the pins allow for the disc space to be compressed by attaching a distractor/compressor system to the superior tip of the pins to create compression across the plate before attaching the screws, thereby enhancing the likelihood of a successful fusion. If needed, the disc space can also be distracted, after placement of the plate over the pins.

1. Ridged Portion

The distraction/compression pins include a ridged portion to enhance retention of the pin in the slot during placement. The ridged portion may be integral with the pin or may be formed as a separate component, such as in the form of a sleeve that is placed in a space between the bone entry portion and the multi-faceted tool fitting region. When the ridged portion is integral with the pin, it is formed of the same material as the rest of the pin, typically metal. The sleeve is typically formed of an elastomer or polymeric material, such as polypropylene. The ridged portion contains a plurality of ridges, which are configured for mating with similar ridges in the slot to hold the plate in its desired location, prior to and during placement of one or more bone screws.

Once the plate is put into position, the pins can be used to compress the opening prior to securing the screws. This is achieved through the use of the slots at each end of the plates which contain teeth on the surface of the side walls of the slots that are configured to mate with the teeth in the corresponding ridged portion of the distraction pin. In contrast, current systems require removal of the pins prior to placement of the plate and positioning of the screws. Thus, with conventional plates, compression is lost during the interval removal of the pins and placement of the plate and screws.

The ridged portion of the pin generally has a larger diameter than that of the threaded bone entry end. Thus, the ridged portion of the pin also serves as a stop region to prevent over-insertion of the distraction pin.

In preferred embodiments, the outer surface of the ridged portion comprises a plurality of teeth configured to mate with the teeth on the surface of the side walls of the slots in the fusion plate.

In other embodiments, the pins may have additional structural elements for carrying out the compression or distraction function. While the structure of the portions of the distraction pin may vary, the overall function of the distraction pin should remain unaltered. For example, in one embodiment, the ridged portion is integral with the pin, while in other embodiments, the ridged portion is formed from a different material than the rest of the pin. In such embodiments, the pin may contain a polymeric sleeve that serves as the ridged portion. The sleeve contains ridges or teeth and provide tight coupling between the ridged portion of the pin and the teeth in the slot of the fusion plate.

2. Exemplary Distraction Pins

Figures 5A, 5B:
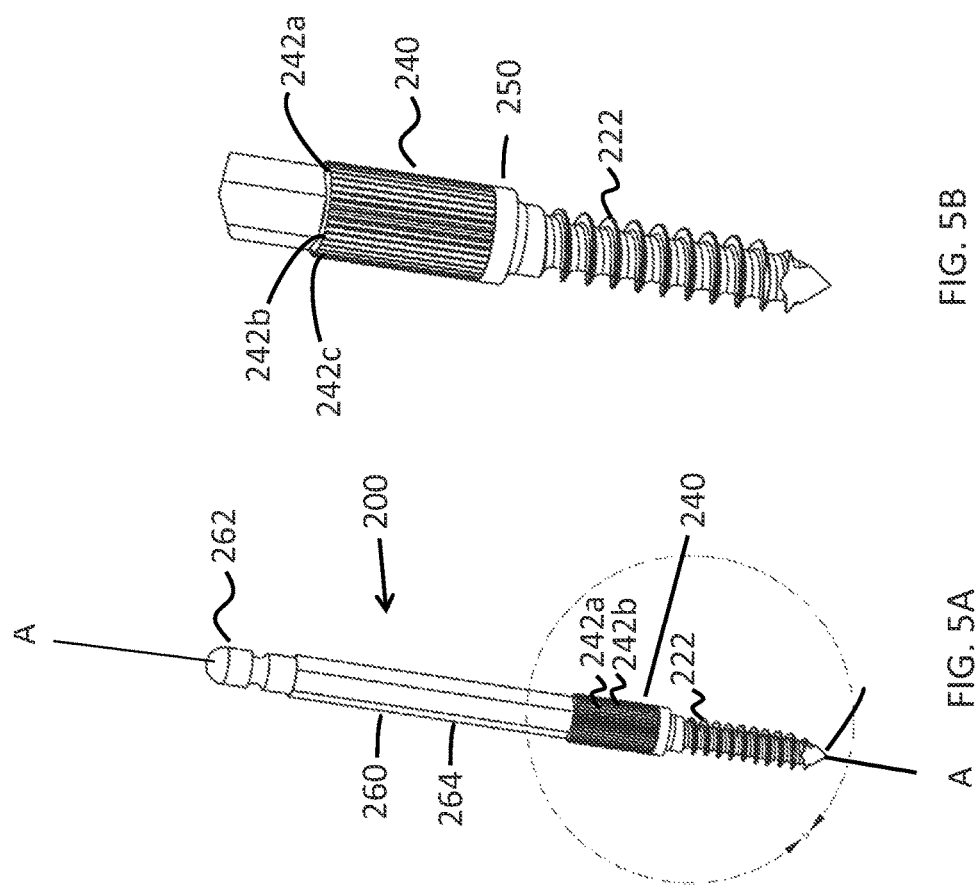
FIGS. 5A and 5B are two views of an exemplary distraction/compression pin.
Figure 6A:
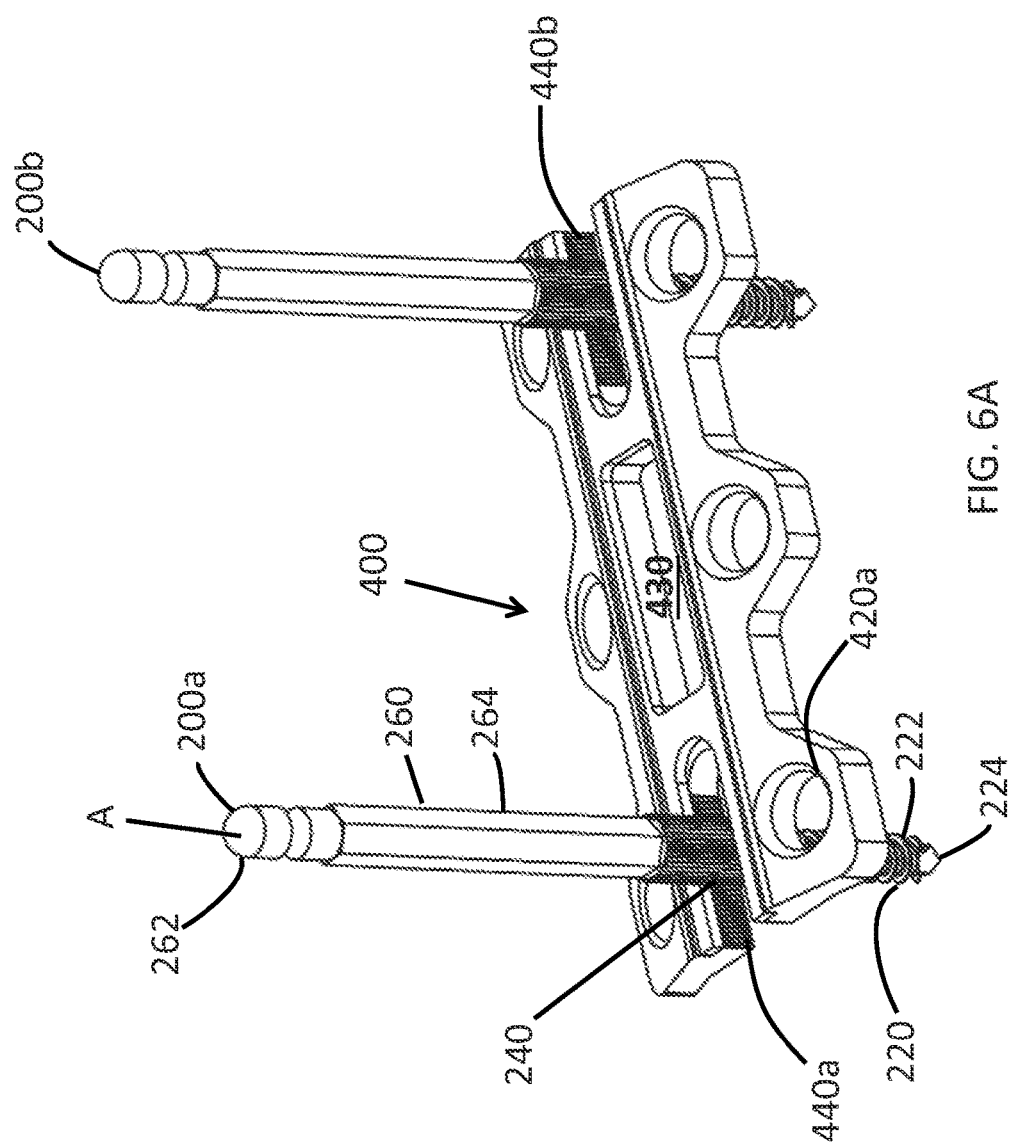
FIGS. 6A and 6B are different views of a two level cervical plate containing two slots and a central window between the slots with two pins in the slots.
Figure 6B:
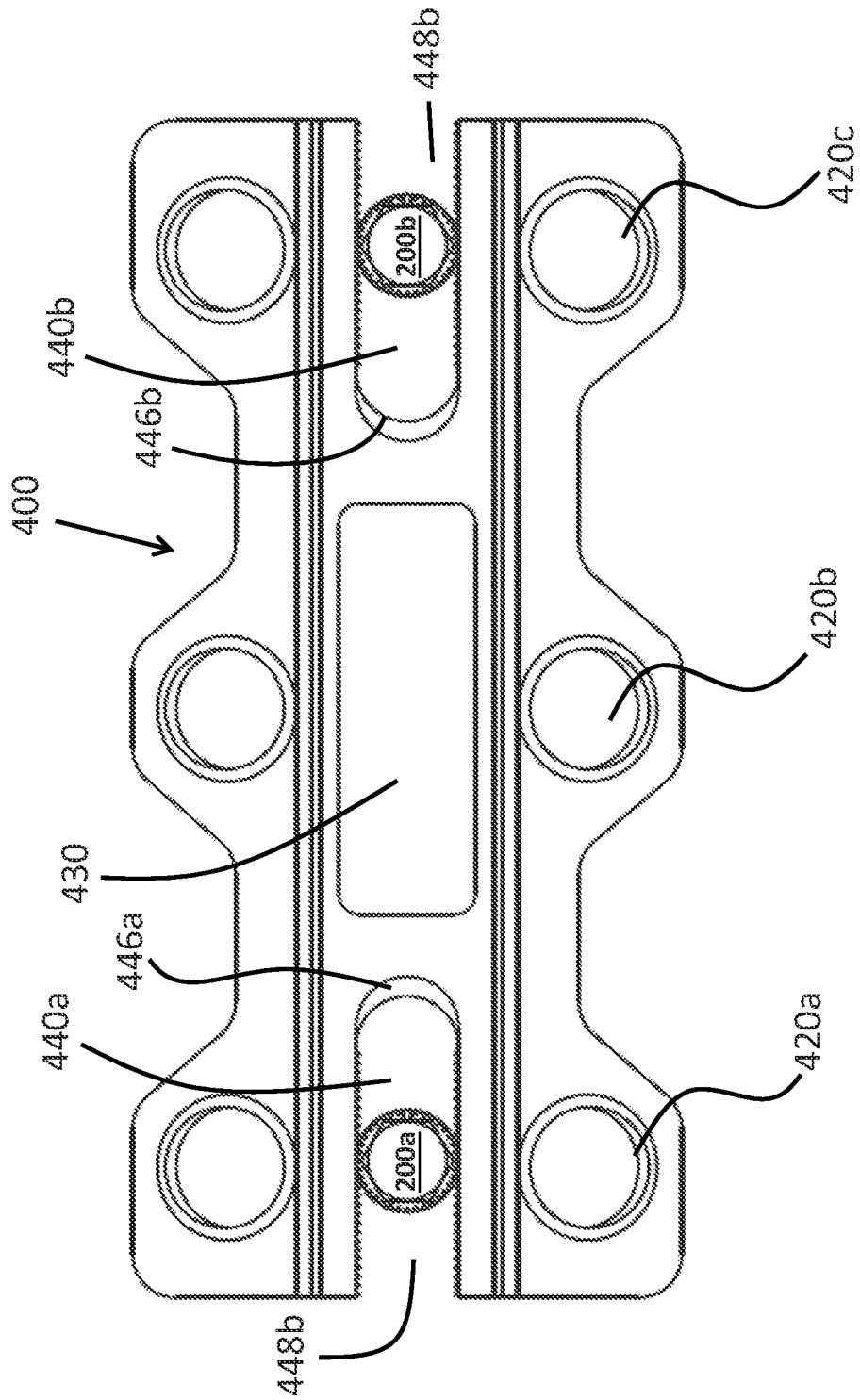
Figure 7A:
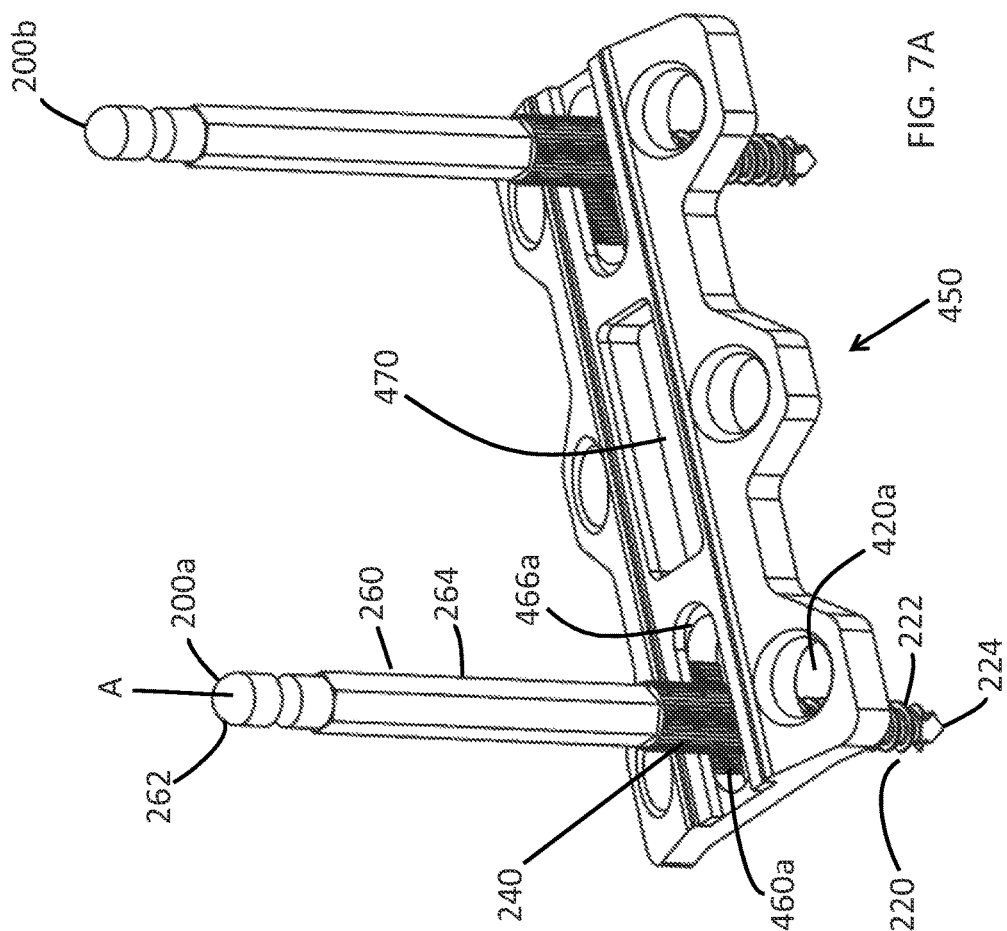
FIGS. 7A and 7B are different views of a two level cervical plate containing two slots, where the slots are closed at both ends, and a central window between the slots with two pins in the slots.
Figure 7B:
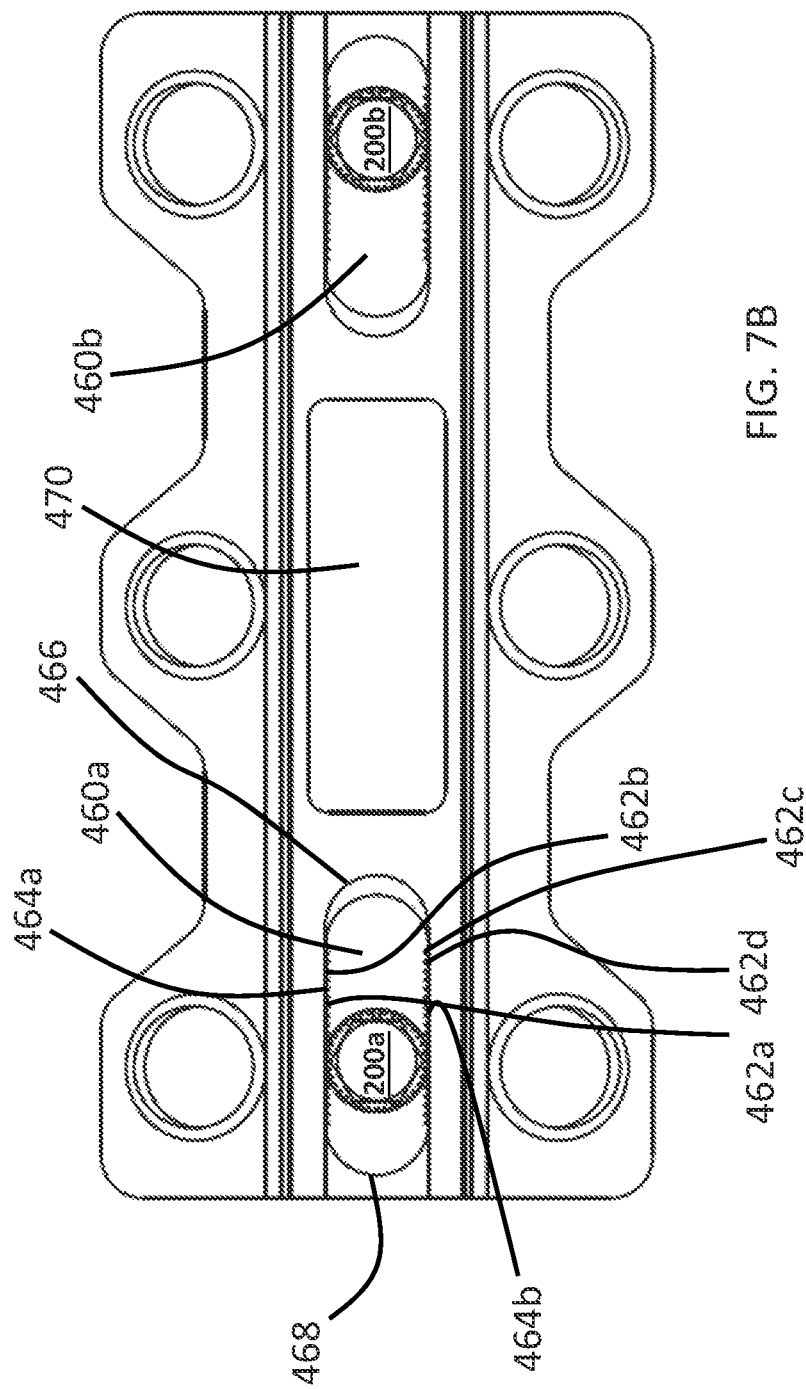

An exemplary distraction pin is depicted in FIGS. 5A and 5B.

The exemplary pin 200 depicted in FIG. 5A-5B has three regions: a threaded bone entry end 220, a ridged portion 240, and a multi-faceted tool fitting region 260.

The tool fitting region 260 of the distraction pin 200 is formed of a superior rounded tip 262 and an elongated body 264 with a hexagonal outer surface.

The outer surface of the ridged portion 240 is formed of mating teeth 242a, 242b, 242c and so on, running parallel to the central axis A of the distraction pin 200. The mating teeth 242a, 242b, 242c and so on mate with the slot teeth 142 of a fusion plate, such as fusion plate 100, 150, 300, or 350, etc., when the cervical plate is placed over the pins.

The threaded bone entry portion 220 of the distraction pin 200 includes outer threads 222, along the central axis A. The threaded portion 220 ends with a sharp inferior tip 224. The threaded portion 220 has a smaller diameter than the ridged portion 240. Thus the transition from the threaded portion to the ridged portion also serves as a stop region 250 to prevent over insertion of the distraction pin.

C. Optional Features

Optionally the system includes a drill guide. The drill guide for screw placement is designed so that accurate angulation of the drill holes can be referenced from the distraction pins.

II. Kits

Plates, screws and pins are typically provided in a sterile kit or kits.

A kit typically contains a plurality of fusion plates and at least two distraction pins. The plates may be provided in several sizes, typically ranging from 20 to 70 mm. These are used to accommodate different sized bones. The kit also typically contains a sufficient number of bone screws to fill the boreholes in the fusion plate.

The kit may also include tool(s) for placement of the pins and/or screws such as drills, taps, and drivers.

III. Methods of Using the Plate and Pin System

The anterior cervical plate and distraction/compression pin system described herein can be used in the cervical spine. The plates may be used to stabilize the cervical spine and promote successful bony fusion, typically following a discectomy (spinal disc removal) or for immobilizing the area surrounding a corpectomy (removal of an entire vertebral body).

The system and method uses distraction pins to properly guide the fusion plate to a centered positioning upon a patient's spine. Once guided onto the spine, the fusion plate is anchored with bone screws.

In the preferred embodiment, the method of using the plates and pins described herein is as follows:

1) Place distraction pins in vertebrae;
2) Use a distractor/compressor system to push pins apart (i.e., distract) to expand the disc space(s);
3) Remove the disc(s);
4) Identify appropriate sized bone graft(s) or cage(s);
5) Place the bone graft(s) or cage(s) into the disc space;
6) Remove the distractor/compressor system but not the pins;
7) Select an appropriately sized plate that is defined by the space between the pins;
8) Place the plate into position with the pins;
9) Apply the distractor/compressor system to compress the disc space;
10) Secure the plate with four or more bone screws; and
11) Remove the distraction pins.

These steps are described in more detail below.

A. Place Distraction Pins in Vertebrae

In step 1 recited above, the pins are inserted into the placement tool and screwed into the vertebral bodies. The pins are inserted up to the stop region of the pins (i.e. prior to the sleeve or ridged portion). The distraction pins are centered on the spine using anatomical landmarks, such as the longis colli muscles or uncinate processes.

B. Using a Distractor System to Push Distraction Pins Apart and Distract the Disc Space In steps 2-6 recited above, typically, the pins can be distracted by pushing the pins apart using a supplemental distractor system. This distraction expands the disc space and holds this expanded space in place during disc removal.

Following disc removal, a spacer or fusion cage containing bone graft material or an allograft spacer is placed in the expanded disc space in between vertebrae. The distractor system is then used to bring the pins closer together and apply compression onto the fusion cage across the disc space. The distractor system is then removed but the distraction pins remain in the vertebral bodies.

C. Selecting an Appropriate Sized Fusion Plate

Then, the physician typically selects an appropriately-sized fusion plate for fixation to the vertebral bodies. The properly sized fusion plate typically bridges the affected segments without overhanging into adjacent disc space. The properly sized fusion plate also has slots positioned at a distance that matches the distance between the reference positions of the distraction pins. Two, or more distraction pins may be used; the number of pins is dependent on the length of the fusion plate.

D. Placing and Securing the Fusion Plate onto the Pins

The selected fusion plate is then lowered onto the vertebrae so that the slot teeth of the fusion plate mate with the corresponding teeth of the pins. In this configuration, the fusion plate is secured superior-inferiorly as it is temporarily locked between its slot teeth and the corresponding teeth of the pins. The plate cannot move in superior-inferior direction unless the distraction pins are compressed or distracted with the distractor/compressor system. The fusion plate is also secured anterior-posteriorly and cannot move unless the plate is moved along the mating teeth of the pins.

In step 8 recited above, the plate in placed over the pins such that one of the pins contacts each of the slots in the plate. As shown in the Figures, the plurality of teeth in the middle region, i.e. the ridged portion, of the distraction pins contact and grip the corresponding teeth located on the side walls of the slots in the fusion plate. The plate is then positioned with the pins holding the plate in place.

E. Compression of the Disc Space Using Pins and Plate

Preferably, the distractor/compressor system is again attached to the distraction/compression pins to compress the disc space. This ensures that the fusion site is compressed across the disc space while the fusion plate is in place and improves spinal fusion. During this step, the distractor/compressor system typically pushes the pins closer together, so that they move from a first position in the slot to a second position in the slot. In each position, the teeth in the pin rest between two corresponding teeth in the slot so that the pin remains in place when a force is not being applied using the distraction/compression system.

F. Insertion of Bone Screws to Secure the Fusion Plate

As described above, the fusion plate is secured from movement in all three dimensions. This allows the surgeon to free both hands and attend to securing the plate to the bones with the bone screws knowing that the plate will not be moved from its original position. Screw holes are drilled and then the screws inserted through the boreholes into the screw holes. The screws may have any suitable configuration, such as self-drilling or self-tapping screws, with cutting or blunt tips. A locking mechanism is typically activated to prevent removal of the screws over time. Any suitable locking mechanism can be used to secure the screws in the boreholes. A variety of bone screw locking mechanisms are well-known.

G. Removal of Distraction/Compression Pins

Following securement of the fusion plate to the vertebral bones via bone screws, the distraction/compression pins are removed. The fusion plate is thus able to hold and preserve the compression across the disc space at the place of its securement, when the distraction pins are removed.

Optionally, after the pins are removed, the remaining holes are filled with bone wax or another sealant to prevent bleeding.

Modifications and variations of the pins and fusion plates and methods of use thereof will be obvious to those skilled in the art and are intended to come within the scope of the appended claims.

I claim:

1. A cervical fixation plate and distraction pin system comprising
   two or more distraction pins, and
   a cervical fixation plate comprising
      two or more boreholes for insertion of screws to position and secure the plate on the vertebral surfaces, and
      two or more slots for placement of the two or more distraction pins,
   wherein one of the slots is located at the inferior end of the plate and another of the slots is located at the superior end of the plate,
   wherein each of the slots comprises two parallel straight side walls, and each of the slots is elongated along a longitudinal axis extending along a centerline of the plate, and wherein at least a portion of each of the side walls is ridged and contains a plurality of teeth, wherein the teeth are configured to mate with and secure the plate to a respective one of the pins and are configured to create and maintain compression across a disc space prior to and during securing of the plate on the vertebral surfaces,
   wherein two of the boreholes are aligned along an axis substantially parallel to the longitudinal axis, the two boreholes disposed laterally with respect to each of the slots, and
   wherein each pin comprises a threaded bone entry end and a ridged portion configured to retain the pin in the respective one of the two or more slots to secure the plate to the vertebral surfaces before attaching the screws, and wherein each pin is configured for removal from the respective one of the two or more slots.

2. The system of claim 1, wherein each slot in the plate further comprises an open end.

3. The system of claim 1, wherein each slot in the plate further comprises a first and a second curved wall connecting the two side walls.

4. The system of claim 1, wherein each pin further comprises a tool fitting region, and wherein the ridged portion is located between the bone entry end and the tool fitting region.

5. The system of claim 4, wherein the ridged portion in each pin is in the form of a sleeve, wherein the sleeve is constructed from an elastomer or polymeric material that comprises a plurality of teeth configured to mate with the corresponding plurality of teeth in the respective slot of the plate.

6. The system of claim 4, wherein the ridged portion is integral with the rest of the distraction pin and comprises a plurality of teeth configured to mate with the corresponding plurality of teeth in the respective slot of the plate.

7. The system of claim 1, wherein the plate further comprises a third slot located substantially in the middle of the plate between the slots at each end of the plate.

8. A method for stabilizing vertebrae in an individual in need thereof comprising:
   providing a distractor/compressor system comprising two or more distraction pins,
   providing a cervical fixation plate comprising
      two or more boreholes for insertion of screws to position and secure the plate on the vertebral surfaces, and
      two or more slots for placement of the two or more distraction pins, wherein each of the slots comprises two parallel straight side walls, and each of the slots is elongated along a longitudinal axis extending along a centerline of the plate,
      wherein each of the two or more slots are ridged to secure the plate to the pins to create and maintain compression across the disc space prior to and during anchoring of the plate before to the vertebral surfaces" now reads "wherein at least a portion of each of the side walls is ridged and contains a plurality of teeth, wherein the teeth are configured to mate with and secure the plate to a respective one of the pins and are configured to create and maintain compression across a disc space prior to and during securing of the plate on the vertebral surfaces
      wherein each of the two or more slots allows removal of the respective pin after the plate is secured with screws,
      wherein two of the boreholes are aligned along an axis substantially parallel to the longitudinal axis, the two boreholes disposed laterally with respect to each of the slots, and
   wherein each of the two or more distraction pins comprises a threaded bone entry end and a ridged portion configured to retain the pin in the respective one of the two or more slots to secure the plate to the vertebral surfaces before attaching the screws.

9. The method of claim 8 comprising
placing the distraction pins in vertebrae;
using the distractor/compressor system to expand the disc space;
removing the disc;
placing an appropriately sized bone graft or cage into the disc space;
removing the distractor/compressor system but not the pins;
placing an appropriately sized plate into position over the pins;
applying the distractor/compressor system to compress the disc space;
securing the plate; and
removing the distraction pins.

* * * * *